Figure 6:
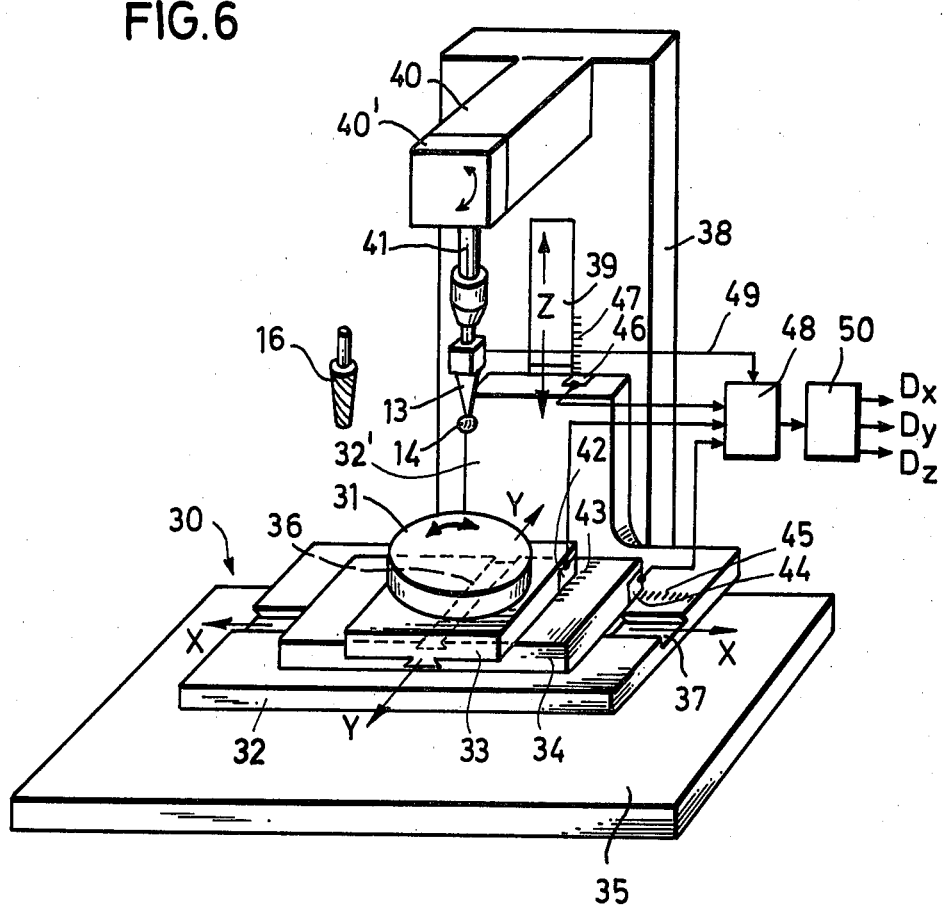

United States Patent [19]

Becker et al.

[11] 4,411,626
[45] Oct. 25, 1983

[54] PROCESS AND APPARATUS FOR PREPARING A CROWN PORTION TO BE FIXED ON A TOOTH

[75] Inventors: Günter Becker, Aachen; Horst Weiden, Stolberg, both of Fed. Rep. of Germany

[73] Assignee: Becker Dental-Labor GmbH, Aachen, Fed. Rep. of Germany

[21] Appl. No.: 223,685

[22] Filed: Jan. 9, 1981

[30] Foreign Application Priority Data

Jan. 31, 1980 [DE] Fed. Rep. of Germany ....... 3003435

[51] Int. Cl.$^3$ ............................................... A61C 5/10
[52] U.S. Cl. ................................................... 433/223
[58] Field of Search ................................. 433/223, 76

[56] References Cited

U.S. PATENT DOCUMENTS 2,793,569  5/1957  Tanner et al. ......................... 433/76
3,058,216  10/1962  Cohen .................................. 433/223

*Primary Examiner*—Robert Peshock
*Attorney, Agent, or Firm*—Spensley, Horn, Jubas & Lubitz

[57] ABSTRACT

An apparatus and process for use in preparing a crown portion to be affixed on a tooth stump is described. A model of the tooth stump is clamped to remain immobile and scanned with a scanning head attached to a numerically controlled processing machine. Data from the scanning head indicative of the contour of the tooth stump is stored in a computer memory. From this data a contour for a casting model used to make a crown portion is calculated and stored in the computer memory. Molding material, such as wax, is placed on the tooth stump and a contour tool attached to the numerically controlled processing machine processes the molding material to produce the casting model using the calculated data. The casting model may then be used to produce a crown portion which may be further finished with a contour tool coupled to the numerically controlled processing machine using the calculated data from the computer memory.

10 Claims, 8 Drawing Figures

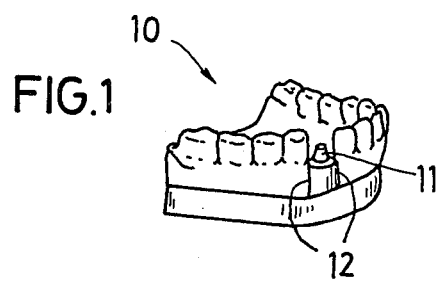
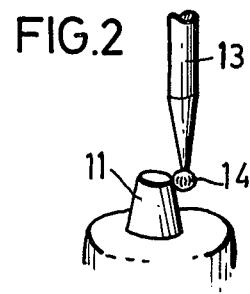
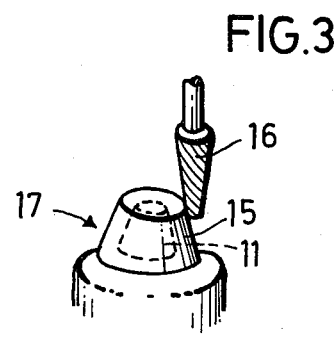
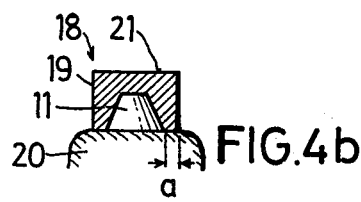
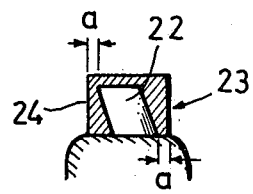
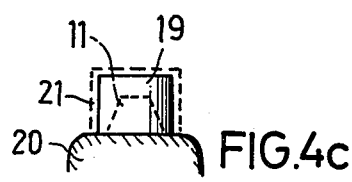

PROCESS AND APPARATUS FOR PREPARING A CROWN PORTION TO BE FIXED ON A TOOTH

The invention relates to a process for preparing a crown portion to be fixed on a tooth stump comprising
(a) making a model of the tooth stump,
(b) applying a molding material to the model
(c) forming the outer contour of the molding material by removal of material and
(d) removing the molding material from the model and using it as a casting model for the crown portion as well as an apparatus for performing the process.

When crowns are prepared for artificial denture, the dentist normally, first of all, is grinding the tooth to be replaced thus producing a tooth stump to secure thereto later the crown portion. Subsequently, a plaster cast is made of the total row of teeth including the ground tooth stump and a plaster model of the row of teeth is prepared therefrom, from which individual teeth may be separated by vertical saw cuts to be processed individually. Then, wax is applied as molding material on the plaster model of the tooth stump. The wax is processed in accordance with the tooth to be replaced, by means of a contour tool, e.g. a milling tool. It is to be ensured in such an operation that a specific minimum wax layer thickness is maintained on all peripheral parts of the tooth stump. It being impossible for the dentist, when milling the wax, to see how thick the wax layer is in individual points, this operation requires a great deal of experience and sensitivity. The wax model produced this way is removed from the tooth stump and used as a casting model for the dental crown portion. The dental crown portion will be made from a high quality material, e.g. from gold.

A similar operation takes place for the preparation of telescopic crowns. To this effect, a primary element, e.g., one made of gold, is secured to the tooth stump and is accurately adapted thereto. A secondary member is placed on the primary element. It carries the artificial tooth and may be also made of gold.

The preparation of such crown portions does not only call for a great experience of the dental technician whose performance must be extremely accurate, but due to the high-quality crown material, the material cost is very high in case of an insufficient working result.

It is the object of the invention to develop a process of the kind disclosed at the outset hereof so that it is ensured in processing of the molding material applied to the tooth stump model that all points of the tooth stump surface are covered with a molding material layer of sufficient thickness.

To solve said problem, it is provided according to the invention that
(a1) the contour of the tooth stump is scanned at least partly to be converted into geometrical data,
(a2) the geometrical data are supplied to a memory,
(a3) from the geometrical data, the contour of the casting model is calculated by considering material allowances on the total outer surface of the tooth stump,
(c1) and according to the calculated contour of the casting model, a contour tool is guided along the molding material applied on the model of the tooth stump.

The contour of the tooth stump is scanned and the contour data is stored. This data is preserved and accessible when the tooth stump is coated with a layer of molding material, e.g. of wax, which is processed by considering the contour data the tooth stump beneath the molding material to ensure that the molding material layer is not removed too much to become too thin. On the other hand, when the primary element of a secondary crown is prepared, it can be also ensured that the material thickness of the casting model—and that of the dental crown portion to be made therefrom—is not greater than absolutely necessary. Hence, the crown portion gets an optimum wall thickness sufficiently strong at all points of the tooth stump surface, but not stronger than necessary anywhere. The very difficult molding operation concerning the casting model (wax model) thus is automated at least partly. By the automatic operation, waste work is avoided and, moreover, it is ensured that no more gold is used for the crown portion than absolutely necessary.

If, for the preparation of the primary element of a telescopic crown, the primary element has been cast in accordance with the shape of the casting model, the outer surface of the primary element must be still superfinished or smoothed to eliminate casting defects. Said superfinishing may be carried out by taking into account the stored shaping data of the tooth stump, i.e., the crown portion produced pursuant to the casting model is placed on the model of the tooth stump, and, subject to the calculated contour of the casting model, however, with a slight reduction in size, it is superfinished. In this respect, it is particularly favorable for the crown portion to be subjected to a material reduction which is constant at all points of its surface. This cannot be realised with manual treatment. Thus, rough sites and defects are eliminated on the surface of the crown portion, which will be accurately adapted to the tooth stump form on which it shall be mounted.

This does not mean, however, that the outer surface of the crown portion will extend in parallel to the outside surface of the tooth stump. If the tooth stump is in inclined position within the row of teeth, its lateral faces are prepared to have parallel edges so that the artificial denture is adapted by mounting it in parallel relative to the other teeth in the mouth and, if necessary, it can be also removed again this way.

An apparatus for performing the process of the invention is characterized in that a numerically controlled processing machine is provided with a clamping device for the model of a group of teeth or a tooth stump and in that it comprises a scanning head as well as a guiding means for guiding the scanning head along the tooth stump, the scanning head being connected to a memory which stores the position data generated when the scanning head is guided along the tooth stump, and in that, in place of the scanning head or in addition thereto, a contour tool is provided which, subject to the contents of the memory controlled by a computer is movable relative to the tooth stump.

Prior to a processing operation, the scanning head is first guided along the tooth stump to feed the surface data thereof into the memory. Subsequently, the molding material is applied to the tooth stump and is processed automatically. During said operations, the tooth stump model remains immobile in the clamping device, with the resulting advantage that the zero point selected during the scanning or predetermined by the processing machine need not be adjusted or converted to fit into another system of coordinates.

In the processing machine, the scanning head and the contour tool must be able to be guided and moved relative to the workpiece. It is irrelevant in this connection as to whether the workpiece is stationary while the scanning head or the contour tool are moved or vice versa, whether the workpiece (model) is moved in a spatial system of coordinates and the scanning head or contour tool are stationary.

In a suitable embodiment of the invention, for the receipt of the contour data of the tooth stump, the scanning head is provided with a contact sensor allowing only the storage of position data in the memory when the scanning head contacts an object thus ensuring that position data are only fed into the memory if the scanning head is in contact with the model to be scanned.

An embodiment of the invention will be explained more closely hereinafter with the reference to the Figures.

FIG. 1 is a perspective view of a plaster model of a lower jaw with a ground tooth stump, FIG. 2 shows the scanning of the outer contour of the tooth stump, FIG. 3 shows the milling of a wax layer applied to the tooth stump, FIGS. 4a, b and c illustrate different phases during the preparation of the crown portion, FIG. 5 is a wax model of a crown portion on an oblique tooth stump, and FIG. 6 is a schematic view of a processing machine for processing operations.

For the preparation of an artificial denture, a plaster model 10 as illustrated in FIG. 1 is made of the corresponding row of teeth in a manner known per se. Prior to the preparation of the plaster model, the tooth which shall be replaced, was ground off in the mouth of the patient. The model of the tooth stump is shown in FIG. 1 and designated with the reference numeral 11. In the plaster model 10 of FIG. 1, individual teeth may be separated by vertical saw cuts 12 so that they may be treated separately.

The plaster model 10 is secured to a processing machine with a clamping device. The processing machine is provided with a scanning pin 13 having a scanning head 14 at its end. The scanning head 14 is now moved along the outer surface of the tooth stump 11. This may be realised for instance in that the scanning head 14 is guided in sequential cycles of different heights about the tooth stump 11. It is also possible to manually guide the scanning head 13 so that the scanning head 14 is scanning the surface of the tooth stump 11. To this effect, the corresponding position of the scanning head 14 is determined by a coordinate guiding device and is fed into a memory. Upon termination of scanning, the memory contains the geometrical data of the tooth stump surface 11.

Thereafter, a molding material 15, for instance wax, is applied to the tooth stump 11 which is completely covered therewith accordingly.

The scanning pin 13 is replaced by a contour tool, e.g. a miller 16, which may rotate about its axis and which is guided by a computer connected to the memory so that the wax layer 15 is of a constant thickness in all points. The wax model 17, prepared this way on the tooth stump has a constant wall thickness, because the contour data of the tooth stump 11 are so processed in the computer that a material allowance is considered and that the miller 16 is then moved by the computer along the calculated outer contour of the wax model 17.

In FIG. 4, the different working steps during the preparation of a crown portion 25 as a primary element of a telescopic crown are illustrated. First off, the tooth stump 11 is scanned and its position data are fed into a memory. Thereafter, the tooth stump 11 is coated with a wax layer from which the wax model 18 is formed in that it gets a circumferential outer wall 19 rising vertically from the jaw 20 to end above the tooth stump 11 with a horizontal front surface 21. As a result of this shaping, the crown portion to be made in accordance with the wax model 18 can be lifted vertically from the jaw 20 even if said crown portion is connected with several artificial teeth in the form of a bridge.

When the wax model 18 is milled, attention should be paid to the fact that a specific minimum thickness a of the wax layer is observed. Moreover, it is another condition that the side walls 19 extend vertically or slightly conically in upward direction.

In accordance with the wax model 18 the crown portion 25 is subsequently cast to be placed on the tooth stump model 11 in accordance with FIG. 4c. The crown portion 25 made of gold is remilled along its outer surface, whereby a removal of material of e.g. 1/10 mm is performed. This superfinishing is achieved also by the numerically controlled processing machine which, as already stated, contains the stored outer contour data of the wax model 18 prepared by it through milling, and superfinishing need be only carried out now with a slightly reduced measure 21.

The plaster model 22 shown in FIG. 5 of a tooth stump is slightly inclined to one side. The wax model 23 of the crown portion to be made also gets parallel vertical walls 24, it being taken care, by the calculation of the wall thickness that the minimum thickness a is not below a determined value in all areas. Thus, the computer calculates the course of the side walls 24 in that the minimum thickness a is not below a minimum thickness in any point whatsoever.

In FIG. 6, a processing machine 30 comprising a clamping device 31 on which the tooth model 10 (FIG. 1) can be secured, is shown, the clamping device 31 being rotatable about a vertical axis and secured to a transverse support 33, which can be moved on a longitudinal support 34 in direction of the Y-axis. The longitudinal support 34, is displaceable on the base plate 35 in direction of the X-axis. The transverse support 33 is conducted in a guide rail 36 extending transversely on the longitudinal support, while the latter is conducted in a guide rail 37 of a vertically displaceable lifter plate 32.

The longitudinal support 34 and the transverse support 33 are provided with (non-illustrated) driving means to move them under control along the guiding rails 37 or 36.

An upright frame 38 is mounted on the base plate 35 and is fitted with a vertical guiding rail 39 in which a vertical guide member 32' of the lifter plate 32 is conducted. The frame 38 has a freely protruding beam 40 from which a rotatorily drivable spindle 41 freely projects downwardly towards the clamping device 31. A scanning pin 13 is secured to the spindle 41.

The transverse support 33 has a position transmitter 42 scanning the line marks 43 provided along the Y-axis on the longitudinal support 34 to determine this way by numerical data the position of the transverse support in direction of the Y-axis.

Just in the same way, the longitudinal support 34 has a position transmitter 44 which is responsive to position marks 45 fitted in parallel to the guide rails 37 at the base plate 35. The position transmitter 44 thus determines the position of the longitudinal support 34 in longitudinal direction.

A third position transmitter 46 is fitted at the guide portion 32'. Said position transmitter 46 is responsive to the position marks 47 fitted in parallel to the guiding rail 39 along the frame 38 to determine the position of the lifter plate 40 and the position of the scanning head of the scanning pin 13 in Z-direction accordingly.

The position data of all three position transmitters 42,44 and 46 are fed to an electronic memory 48. The data are only supplied to the memory if a contact with any object is sensed at the scanning head. This is reported to the memory 48 via a control line 49.

If the plaster model 10 is secured to the clamping device 31, care is taken by suitable, for instance manual movements of the longitudinal support 34, of the transverse support 33 and of the lifter plate 32 that the scanning head 14 is moved along the surface of the tooth stump 11. By this means, the X,Y and Z data are recorded in the memory 48 for each point of contact or each surface point of the tooth stump. Due to said position data, a picture of the outer surface of the tooth stump is formed in the memory 48.

The memory 48 is connected to a computer 50 which calculates from the determined outer contour of the tooth stump the outer contour of the wax model to be prepared while considering the given marginal conditions, e.g. a minimum material thickness a or the vertical or conical extension of the side walls of the wax model.

Then, the scanning pin 13 is replaced by miller 16 which is mounted at the spindle 41 which is caused to rotate. Computer 50 supplies the position values $D_x$ re the position of the transverse support 33, $D_y$ re the position of the longitudinal support 34 and $D_z$ re the vertical position of the lifter plate 32. Said position data are changed in that the miller 16 is moved along the desired contour of the wax model until the latter has acquired the outer contour determined by the computer 50. To adjust the positions, the signals of the position transmitters 42,44 and 46 are also supplied as feed-back signals to the controller 50.

Basically, the three coordinate values X,Y and Z are sufficient for the numerical determination of the outer contour of a workpiece. To ensure that the scanning head 14 and the miller 16 are conducted to points which are of difficult access, the front end 40' of the beam 40 can be pivoted about the horizontal longitudinal axis of the beam so that the spindle 40 can be swivelled out of its vertical basic position. Moreover, the clamping device 31 can be supported pivotally about a vertical axis. The rotary or swivel positions of parts 40' and 31 can be also sensed by position feelers to be supplied to the memory 48 or to the counter 50.

What is claimed is:

1. In a process for preparing a dental crown portion to be secured to a tooth stump in which a model is made of the tooth stump, molding material is applied to the model and has its outer contour formed by removal of material, said molding material being thereafter removed from the model and used as a casting model for the dental crown portion, the steps of:
    scanning with a scanning head for conversion into geometrical data at least part of the contour of the tooth stump;
    supplying the geometrical data to a computer memory coupled to the scanning head;
    calculating, from the geometrical data, the contour for the casting model, taking into account an allowance for material on the outer surface of the tooth stump and storing said data in the computer memory; and,
    guiding, according to the calculated contour for the casting model, a contour tool coupled to the computer memory along the molding material that has been applied to the model of the tooth stump whereby a casting model for a dental crown portion is formed.

2. The steps of claim 1, including the additional steps of;
    placing the dental crown portion produced from the casting model on the tooth stump model; and
    guiding a contour tool coupled to the computer memory on said casting model in accordance with the calculated contour of the casting model, reduced a slight measure in order to super-finish said dental crown portion.

3. An apparatus for use in preparing a dental crown portion to be secured to a tooth stump, said apparatus using a numerically controlled processing machine and comprising:
    a clamping device on said processing machine for a model of a group of teeth containing a tooth stump or for a model of a tooth stump;
    a scanning head on said processing machine for generating position data;
    a guiding means on said processing machine for guiding the scanning head along said model;
    a computer memory connected to said scanning head for storing position data generated when the scanning head is guided along the model; and
    a contour tool on said processing machine controlled by said memory and movable relative to said model.

4. An apparatus according to claim 3 wherein the scanning head has a contact sensor which only allows the storage of position data in the computer memory when the scanning head contacts another object.

5. Apparatus for the preparation on a blank of a copy from an original object comprising:
    a numerically controlled processing machine having a scanner for generating position data of the surface of the original object;
    an electronic control device having a memory for storing said position data; and
    a processing tool connected to said electronic control device and guided along a blank in accordance with the stored position data to reproduce the surface of the original object.

6. A process for producing from molding material on a tooth stump model a casting model for a dental crown, said casting model having a specified minimum thickness over all parts of the tooth stump model comprising:
    fixedly mounting the tooth stump model relative to a numerically controlled processing machine;
    scanning at least part of the surface of the tooth stump model to acquire data characteristic of the surface contour of the tooth stump model with a scanning head on said processing machine;
    storing said data in a computer memory coupled to said machine;
    applying a molding material to the tooth stump model; and
    moving a contouring device on said processing machine to form a casting model from said molding material using said stored data from said computer memory to control said contouring device.

7. A process for producing a finished dental crown for insertion onto a tooth stump wherein a casting model has been produced according to claim 6 and said casting model has been used to produce the dental crown, comprising:
placing the dental crown on the tooth stump model; and
milling, with a contouring device on said processing machine, said dental crown, said contouring device being controlled by said stored data from said computer memory according to the measure used to form the casting model reduced in size a small amount, whereby rough sites and casting defects are removed from the surface of said dental crown.

8. A process for smoothing the outer surface of a dental crown, said dental crown produced from a casting model in which data characteristic of the surface of the tooth stump on which the dental crown is to be placed has been stored in a computer memory and used to control a contouring device on a numerically controlled processing machine in order to form the casting model from molding material applied to a model of the tooth stump, comprising:
placing the crown portion on the model of the tooth stump; and
milling, with a contouring device on said processing machine, said dental crown, said contouring device being controlled by stored data from said computer memory in order to mill the dental crown according to the measure used to form the casting model, reduced in size a small amount.

9. An apparatus for use in producing a casting model or a dental crown portion for a tooth stump for which a tooth stump model has been made comprising:
means for generating data indicative of the contour of the surface of the tooth stump model;
computer means coupled to said means for generating data for storing said generated data and for calculating from said stored data the outer contour of a dental crown or a casting model;
a contouring device movable relative to said tooth stump model; and
means coupled to said contouring device for moving said contouring device relative to the tooth stump model, said means coupled to and cooperating with said computer means so that material placed on said tooth stump model is formed by said contouring device according to said calculated outer contour into a dental crown or casting model.

10. An apparatus as in claim 9 wherein said means for generating data indicative of the contour of the surface of the tooth stump model comprises:
a contact sensor; and
position transmitting means for transmitting the position of said contact sensor to said computer means when said contact sensor is placed in contact with said tooth stump model.

* * * * *